(12) United States Patent
Yang et al.

(10) Patent No.: US 10,842,906 B2
(45) Date of Patent: Nov. 24, 2020

(54) AIR PURIFILER

(71) Applicant: Jin-Ting Hou, Taipei (TW)

(72) Inventors: Chin-Huei Yang, Taipei (TW);
Yen-Yang Huang, Keelung (TW);
Jin-Ting Hou, Taipei (TW)

(73) Assignee: Jin-Ting Hou, Taipei (TW)

( * ) Notice: Subject to any disclaimer, the term of this patent is extended or adjusted under 35 U.S.C. 154(b) by 203 days.

(21) Appl. No.: 16/209,798

(22) Filed: Dec. 4, 2018

(65) Prior Publication Data
US 2019/0167833 A1 Jun. 6, 2019

(30) Foreign Application Priority Data

Dec. 5, 2017 (TW) .............................. 106218040 U

(51) Int. Cl.
*A61L 9/20* (2006.01)
*F24F 13/20* (2006.01)
*F24F 3/16* (2006.01)
*F24F 13/28* (2006.01)

(52) U.S. Cl.
CPC .............. *A61L 9/20* (2013.01); *F24F 3/1603* (2013.01); *F24F 13/28* (2013.01); *A61L 2209/11* (2013.01); *A61L 2209/12* (2013.01); *A61L 2209/212* (2013.01); *F24F 13/20* (2013.01); *F24F 2003/1614* (2013.01); *F24F 2003/1657* (2013.01); *F24F 2003/1667* (2013.01)

(58) Field of Classification Search
CPC .. A61L 9/20; A61L 2209/14; A61L 2209/212; F24F 13/20; F24F 2003/1667

USPC ............. 55/385.1, 385.2, 471–473, DIG. 34; 96/417, 418
See application file for complete search history.

(56) References Cited

U.S. PATENT DOCUMENTS

| | | | |
|---|---|---|---|
| 2005/0152146 A1* | 7/2005 | Owen | C02F 1/325 362/294 |
| 2006/0177356 A1* | 8/2006 | Miller | A61M 11/06 422/121 |
| 2008/0112844 A1* | 5/2008 | Garrett | A61L 9/205 422/4 |
| 2009/0205664 A1* | 8/2009 | Lyon | B01D 53/007 128/205.12 |
| 2015/0250913 A1* | 9/2015 | Matsui | F24F 3/16 250/436 |
| 2015/0359922 A1* | 12/2015 | Kim | A61L 9/00 422/121 |
| 2019/0111169 A1* | 4/2019 | Flaherty | G06F 3/016 |
| 2019/0127675 A1* | 5/2019 | Adams | C12M 23/16 |
| 2019/0226698 A1* | 7/2019 | Kim | F24F 11/52 |
| 2019/0240370 A1* | 8/2019 | Benedek | F24C 15/205 |

(Continued)

*Primary Examiner* — Minh Chau T Pham
(74) *Attorney, Agent, or Firm* — Chun-Ming Shih; LanWay IPR Services

(57) ABSTRACT

An air purifier includes a upper cover, having at least one grid column on front terminal of the upper cover; a bottom cover, having at least one grid column on front terminal of the bottom cover; and two groups of ultraviolet light emitting diodes (LEDs), respectively having a heat sink and a ultraviolet light emitting diode (LED), wherein the ultraviolet LED is mounted on the heat sink, and a wavelength range of the ultraviolet LED is between 100 nm and 480 nm; wherein the grid column on front terminal of the upper cover is combined with the grid column on front terminal of the bottom cover to form a column hole through which an air flows out.

17 Claims, 6 Drawing Sheets

(56) References Cited

U.S. PATENT DOCUMENTS

2019/0240371 A1* 8/2019 Benedek .............. B01D 46/006
2020/0008394 A1* 1/2020 Chun .................... B01D 46/10
2020/0061231 A1* 2/2020 Jeong ................ B01D 46/0009

* cited by examiner

AIR PURIFILER

BACKGROUND OF INVENTION

1. Field of the Invention

The present invention is related to an air purifier, and more particularly, to an air purifier with air purification, sterilization function, small size and portable can be used for indoor space in the home or space in the car.

2. Description of the Prior Art

According to recent years, due to problems such as exhaust emissions from the vehicles on the road, heavy industry development, and smog, etc., air pollution is becoming more and more serious. The concentration of contaminating particles such as PM2.5 and PM10 often exceeds the standard. The indoor environment will also be affected by serious outdoor air pollution, and when the people return home from the outdoors, they may bring the contaminated particles of the outdoor air home. Sometimes the home is in a closed environment, or the suspended particles in the indoor air can cause poor air quality. Therefore, the air purifier has gradually become one of the home appliances that the people will choose to purchase.

Most of the air purifiers on the market are household appliances. The drawback lies in the fact that the conventional air purifiers are relatively large in size, and they are placed in the home to occupy the indoor space in the home, and are inconvenient to move and carry. Nowadays, the air pollution situation is getting more and more serious. It is not only the indoor environment in the home that needs air purifier to purify the air, but also driving out of the car, the environmental space inside the car also needs an air cleaner to help clean the air. It is not only the indoor environment in the home that needs the air purifier to purify the air, but also needs the air purifier to help clean the air in the environmental space inside the car. Thereby, it is an important research topic that how to reduce the volume of the air purifier, and how to let the air purifier not occupy space and being convenient to carry, and even how to install the air purifier in the space of the vehicle.

Conventional air purifiers, which are generally use filters to filter harmful airborne particles in the air, and do not have ultraviolet sterilization and negative ion functions in same time.

Accordingly, there has a need for developing an air purifier with small size and portability, ultraviolet sterilization and negative ion functions for solving the problem arising from the conventional arts.

SUMMARY OF THE INVENTION

The primary objective of the present invention is to provide an air purifier, which purifies the air and sterilizes, and being with the small size for convenient to carry, and can be placed in the indoor space of the home or the space inside the car for use.

In order to achieve the above-mentioned objectives, the present invention provides an air purifier, comprising: a upper cover, having at least one grid column on front terminal of the upper cover; a bottom cover, having at least one grid column on front terminal of the bottom cover; and two groups of ultraviolet light emitting diodes (LEDs), respectively having a heat sink and a ultraviolet light emitting diode (LED), wherein the ultraviolet LED is mounted on the heat sink, and a wavelength range of the ultraviolet LED is between 100 nm and 480 nm; wherein the grid column on front terminal of the upper cover is combined with the grid column on front terminal of the bottom cover to form a column hole through which an air flows out.

In one embodiment, the wavelength range of the two groups of ultraviolet LEDs is between 100 nm and 280 nm. In one embodiment, the wavelength of one of two groups of ultraviolet LEDs is 260 nm, and the wavelength of another group of ultraviolet LEDs is 280 nm. In one embodiment, the wavelength range of one of two groups of ultraviolet LEDs are between 100 nm and 280 nm, and the wavelength range of another group of ultraviolet LEDs are between 400 nm and 480 nm which is violet-blue light wavelength range. In one embodiment, the wavelength of one of two groups of ultraviolet LEDs is 275 nm, and the wavelength of another group of ultraviolet LEDs is 405 nm which is violet-blue light wavelength range.

In one embodiment, the air purifier further comprising: a filter cover, a filter, a motor, a control module, a power module and a diversion tube, wherein the filter cover, the motor, the control module, the power module and the diversion tube are mounted between the upper cover and the bottom cover, and arranged in sequence toward the column hole, wherein the filter is mounted between the filter cover and the motor, one side of the motor has a suction inlet, the suction inlet is adjacent to the filter, and another side of the motor is adjacent to the diversion tube, wherein the power module and the control module are mounted on outer surface of the diversion tube, the power module has a transformer, and the power module electrically connects to the control module and the motor, wherein two sides of an gap between the filter and the motor respectively has the two groups of ultraviolet LEDs, and the two groups of ultraviolet LEDs electrically connects to the control module.

In one embodiment, the diversion tube has a support and blow hole, the support is adjacent to the motor, and the filter cover has a plurality of filtering holes, and inside of the filter consists of a plurality of filter films.

In one embodiment, the control module further comprises a circuit board and a control board, and the circuit board comprises a plurality of light emitting diodes, a plurality of buttons, at least one connector and a switch, and the control board electrically connects to the circuit board and the motor, the control board comprises a connector, the connector of the control board is electrically connected to the connector of the circuit board, and wherein there are many the light emitting diode holes correspond to the light emitting diodes mounted on the upper cover, and there are many button holes correspond to the buttons mounted on the upper cover.

In one embodiment, the circuit board further comprises a negative ion generator, the negative ion generator is arranged in inside of the diversion tube, and the negative ion generator electrically connects the circuit board.

Thereby, when the motor is in operation, external air enters into the air purifier through the filter cover, and the air is filtered through the filter, and the filtered air flows out from the diversion tube to the column hole to discharge clean air. Therefore, the effect of purifying air and sterilizing can be achieved.

The another objective of the present invention is to provide an air purifier, which purifies the air and sterilizes has a bag, and the air purifier with the bag is fixed in a chair back of a car chair so as to achieve the purpose of using an air purifier in the space inside the car.

In order to achieve the above-mentioned objectives, the present invention provides an air purifier, comprising: a upper cover, having at least one grid column on front terminal of the upper cover; a bottom cover, having at least one grid column on front terminal of the bottom cover, wherein the grid column on front terminal of the upper cover is combined with the grid column on front terminal of the bottom cover to form a column hole through which an air flows out; two groups of ultraviolet LEDs, respectively having a heat sink and a ultraviolet LED, wherein the ultraviolet LED is mounted on the heat sink, and a wavelength range of the ultraviolet LED is between 100 nm and 480 nm; and a bag, having a hole, and a place in the hole, and the place inside correspond to the upper cover and the bottom cover, and a plurality of through holes arranged on a surface of the bag, the through holes connecting to the place, and the air flowed out through the through hole to the outside of the bag, and wherein there is a fixed element mounted on outer surface of the bag, and the fixed element fixes the bag on a chair back of a car chair.

In one embodiment, the fixed element is selected from one of the flexible band, a clip, a rope or a velcro.

In one embodiment, the wavelength range of the two groups of ultraviolet LEDs is between 100 nm and 280 nm. In one embodiment, the wavelength of one of two groups of ultraviolet LEDs is 260 nm, and the wavelength of another group of ultraviolet LEDs is 280 nm. In one embodiment, the wavelength range of one of two groups of ultraviolet LEDs are between 100 nm and 280 nm, and the wavelength range of another group of ultraviolet LEDs are between 400 nm and 480 nm which is violet-blue light wavelength range. In one embodiment, the wavelength of one of two groups of ultraviolet LEDs is 275 nm, and the wavelength of another group of ultraviolet LEDs is 405 nm which is violet-blue light wavelength range.

All these objects achieved by oven apparatus according to the present invention are described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
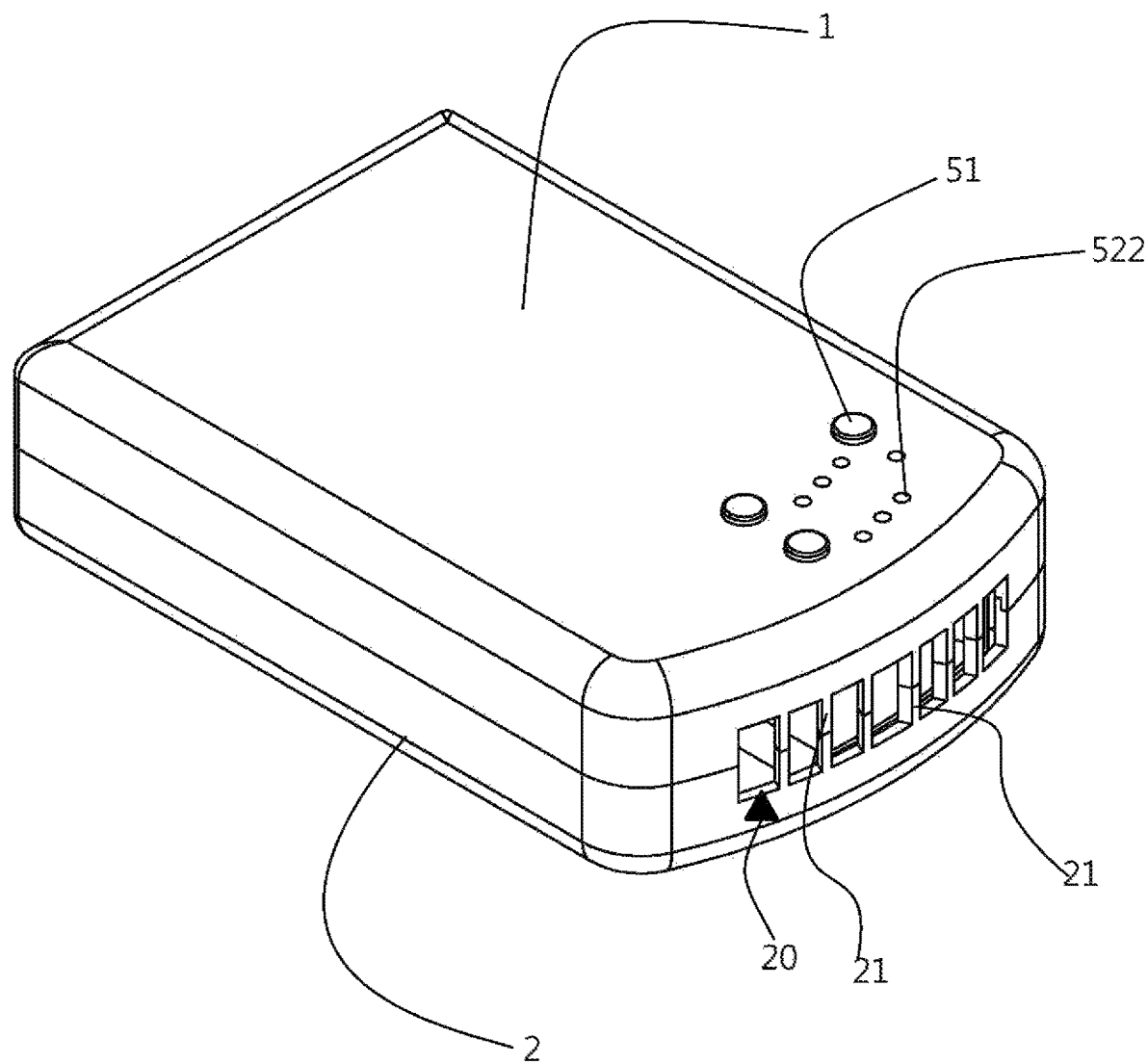
FIG. 1 illustrates an appearance schematic diagram of an air purifier according to one embodiment of the present invention.
Figure 2:
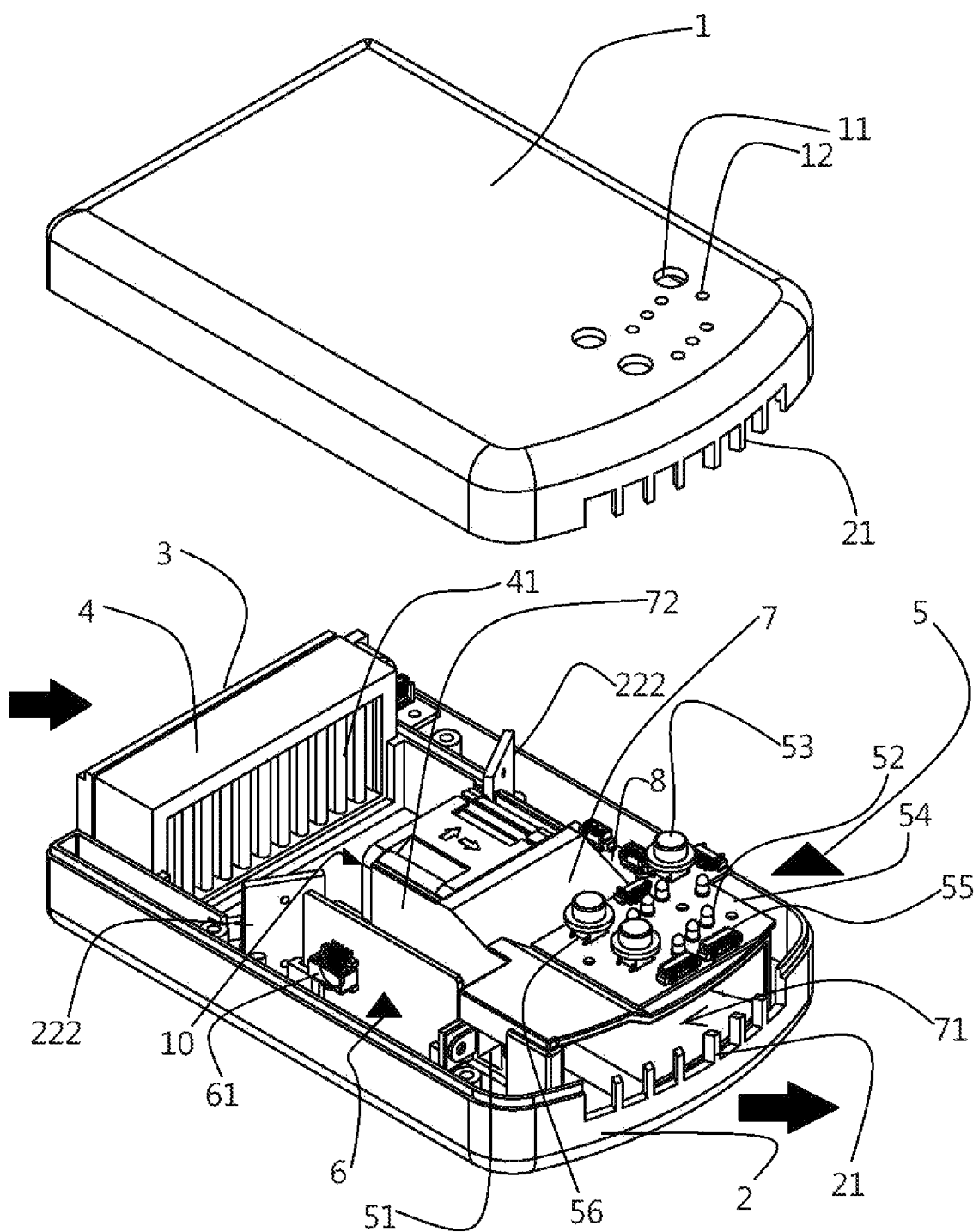
FIG. 2 illustrates an assembly schematic diagram of an air purifier according to one embodiment of the present invention.

The invention disclosed herein is directed to a container with synchronous rising and lowering functions. In the following description, numerous details corresponding to the aforesaid drawings are set forth in order to provide a thorough understanding of the present invention so that the present invention can be appreciated by one skilled in the art, wherein like numerals refer to the same or the like parts throughout.

Although the terms first, second, etc. may be used herein to describe various elements, components, modules, and/or zones, these elements, components, modules, and/or zones should not be limited by these terms. Various embodiments will now be described in conjunction with a number of schematic illustrations. Various embodiments of the application may be embodied in many different forms and should not be construed as a limitation to the embodiments set forth herein.

For clearly understanding the present invention, please refer to the following description as well as FIGS. 1 to 5. In the embodiment, an air purifier comprising: a upper cover 1, having at least one grid column 21 on front terminal of the upper cover 1; a bottom cover 2, having at least one grid column 21 on front terminal of the bottom cover, wherein the grid column 21 on front terminal of the upper cover is combined with the grid column 21 on front terminal of the bottom cover 2 form a column hole 20 through which an air flows out; and two groups of ultraviolet light emitting diodes (LEDs) 22, respectively having a heat sink 222 and a ultraviolet light emitting diode (LED) 221, wherein the ultraviolet LED 221 is mounted on the heat sink 222, and a wavelength range of the ultraviolet LED 221 is between 100 nm and 480 nm which is violet-blue light wavelength range.

Moreover, in the embodiment, the air purifier further comprising: a filter cover 3, a filter 4, a motor 10, a control module 5, a power module 6 and a diversion tube 7, wherein the filter cover 3, the motor 10, the control module 5, the power module 6 and the diversion tube 7 are mounted between the upper cover 1 and the bottom cover 2, and arranged in sequence toward the column hole 20, wherein the filter 4 is mounted between the filter cover 3 and the motor 10, one side of the motor 10 has a suction inlet 101, the suction inlet 101 is adjacent to the filter 4, and another side of the motor 10 is adjacent to the diversion tube 7, wherein the power module 6 and the control module 5 are mounted on outer surface of the diversion tube 7, the power module 6 has a transformer 61, and the power module 6 electrically connects to the control module 5 and the motor 10. Thereby, when the motor 10 is in operation, external air enters into the air purifier through the filter cover 3, and the air is filtered through the filter 4, and the filtered air flows out from the diversion tube 7 to the column hole 20 to discharge clean air. Therefore, the effect of purifying air and sterilizing can be achieved.

Figure 3:
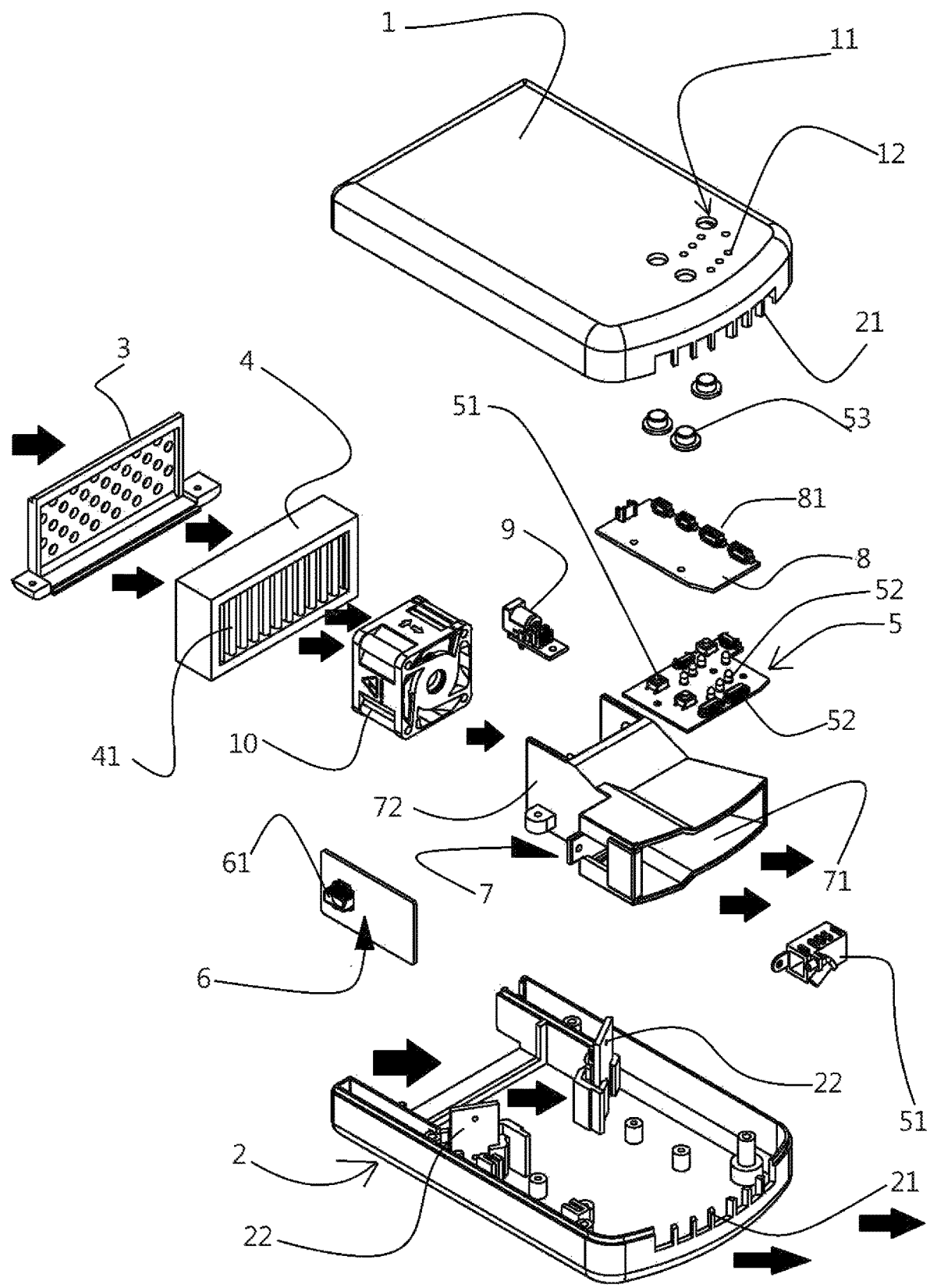
FIG. 3 illustrates an explosion schematic diagram of air purifier according to one embodiment of the present invention.
Figure 4:
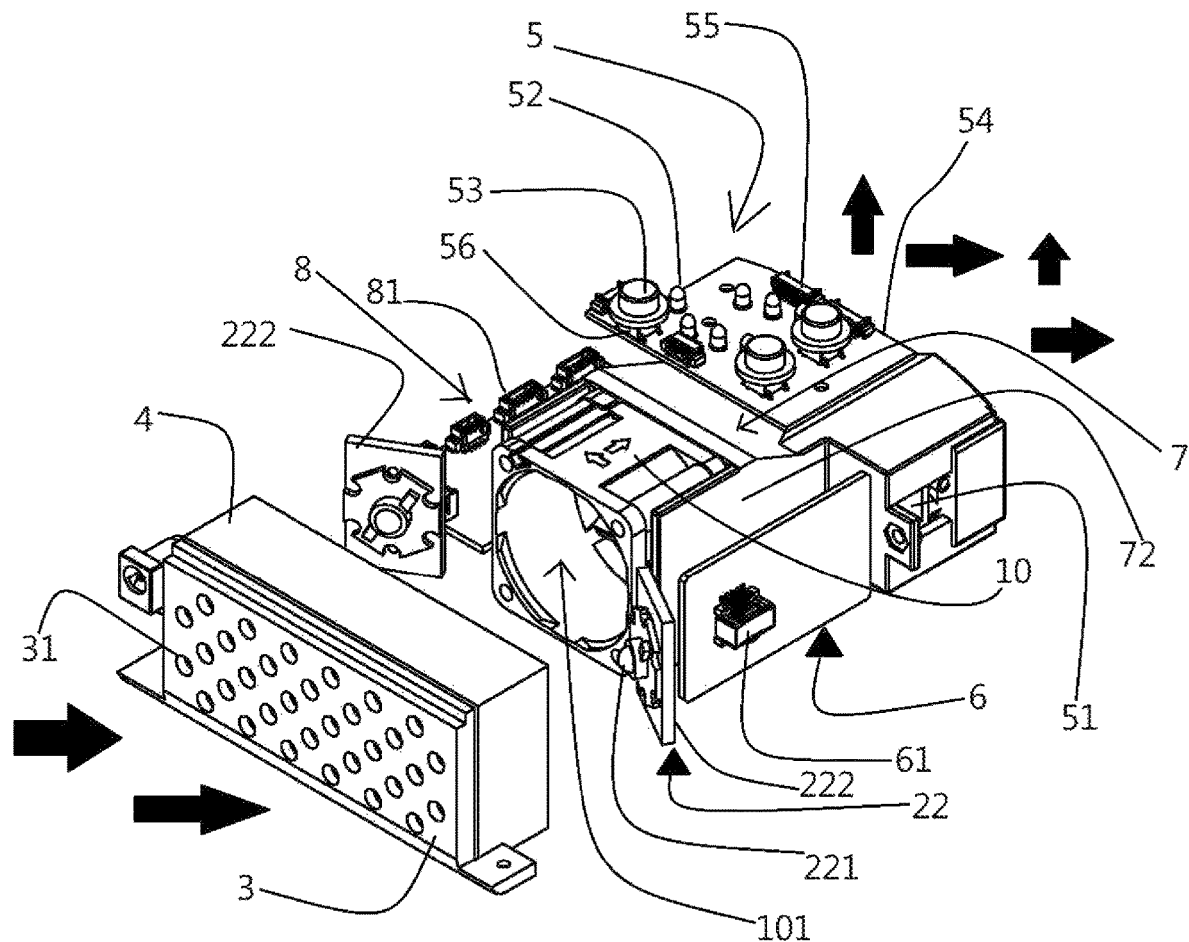
FIG. 4 illustrates an inside rear schematic diagram of an air purifier according to one embodiment of the present invention.
Figure 5:
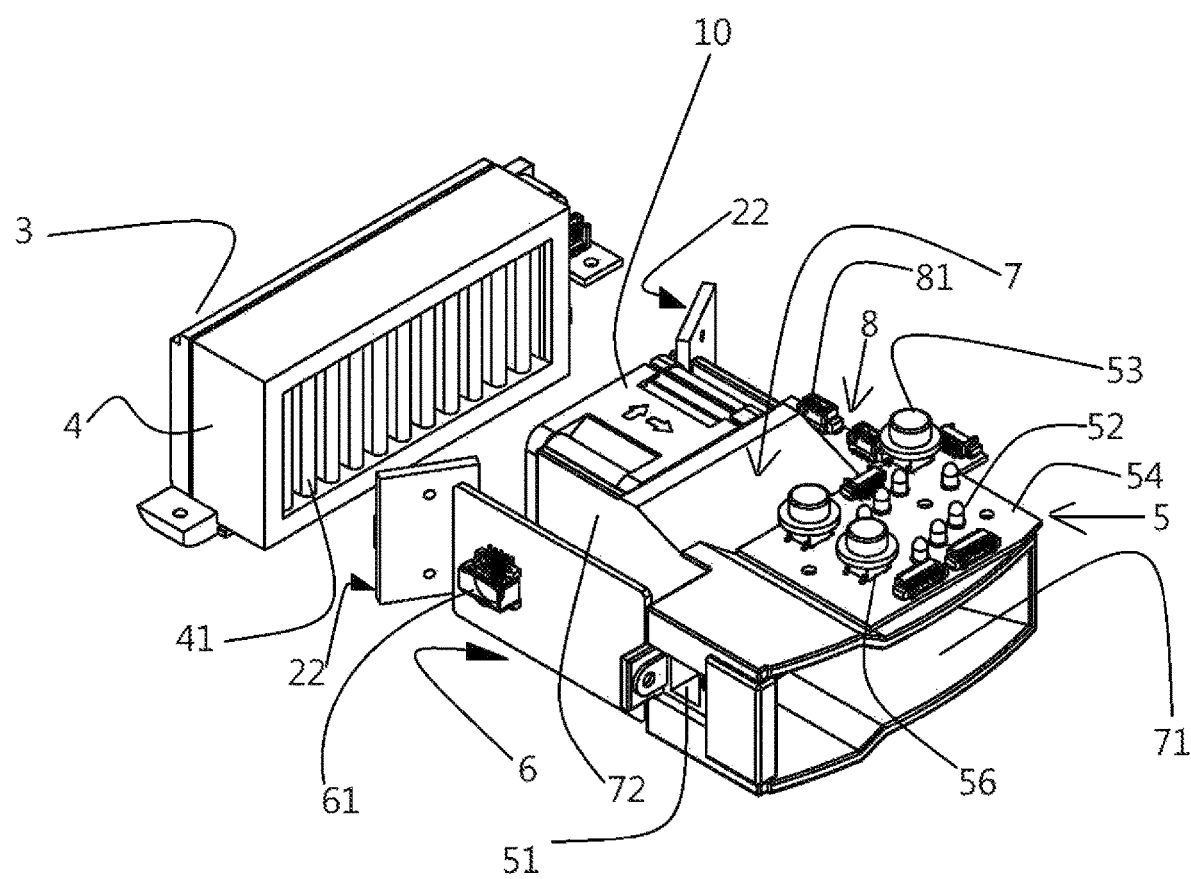
FIG. 5 illustrates an inside front schematic diagram of an air purifier according to one embodiment of the present invention.

Refer to FIG. 3~FIG. 5, which respectively illustrate an explosion schematic diagram, an inside rear schematic diagram of an air purifier, an inside front schematic diagram of an air purifier according to one embodiment of the present invention. Specifically, two sides of a gap between the filter 4 and the motor 10 respectively has the two groups of ultraviolet LEDs 22, and the two groups of ultraviolet LEDs 22 electrically connects to the control module 5. The diversion tube 7 has a support 72 and a blow hole 71, the support 72 is adjacent to the motor 10, and the filter cover 3 has a plurality of filtering holes 31, and inside of the filter 4 consists of a plurality of filter films 41.

Refer to FIG. 3~FIG. 5, a wavelength range of the ultraviolet LED 221 is between 100 nm and 480 nm. In the embodiment, the two groups of ultraviolet LEDs 221 provide a combination of multiple bands. In addition to different killing effects on different types of viruses, bacteria, parasites, pathogens and algae, the wavelengths synergistically enhance generated by the combination of multiple bands can enhance the bactericidal effect. The wavelength range from 100 nm to 400 nm may be the ultraviolet A (UVA), the ultraviolet B (UVB) and the ultraviolet C (UVC). Specifically, the wavelength range of UVA is between 320 nm and 400 nm, the wavelength range of UVB is between 280 nm and 320 nm, and the wavelength range of UBC is between 100 nm and 280 nm. The germicidal band of UVC is effective for killing almost all viruses, bacteria, parasites, pathogens and algae. The wavelength range of the ultraviolet LED 221 between 400 nm and 480 nm is violet-blue light wavelength range which is less harmful to the human body.

In the embodiment, the structure of the two groups of ultraviolet LED 221 is selected from a combination of UVA, UVB or UVC.

In one embodiment, the wavelength range of the ultraviolet LED 221 is a combination of two different bands, one is the band of ultraviolet C (UVC), and another is band being between 400 nm and 480 nm which is violet-blue light wavelength range. The wavelengths synergistically enhance generated by the combination of multiple bands can enhance the bactericidal effect. In one embodiment, the wavelength range of ultraviolet LED 221 is a combination of 275 nm or 405 nm. Two groups of ultraviolet LEDs 221 may be one is 275 nm, and another one is 405 nm which is violet-blue light wavelength range. In addition, two groups of ultraviolet LEDs 221 all are 275 nm, or 405 nm.

In one embodiment, the wavelength range of the ultraviolet LED 221 is a combination of two same bands being a combination of two UVCs. The wavelengths synergistically enhance generated by the combination of multiple bands can enhance the bactericidal effect. In one embodiment, two groups of ultraviolet LEDs 221 may be one is 260 nm, and another one is 280 nm. In addition, two groups of ultraviolet LEDs 221 all are 260 nm, or 280 nm.

In another embodiment, the ultraviolet light emission method of the two groups of ultraviolet LEDs 221 may be the long-lasting UV emission mode, or the pulse UV emission mode, or a combination mode of the long-lasting UV emission mode mixed with the pulse UV emission mode. In addition, the ultraviolet light emission modes of the two groups of the ultraviolet LEDs 221 may also be two sets of alternating pulse mode ultraviolet light emission modes, for example, one of two groups of ultraviolet LEDs 221 is the pulse UV emission mode with the wavelength of 275 nm, and another group of ultraviolet LEDs 221 is the pulse UV emission mode with the wavelength of 260 nm. Specifically, the ultraviolet LEDs 221 being the pulse UV emission mode with the wavelength of 275 is switched "ON" to perform the UV sterilization, and while the ultraviolet LEDs 221 being the pulse UV emission mode with the wavelength of 260 is switched "OFF". Then, the ultraviolet LEDs 221 being the pulse UV emission mode with the wavelength of 275 is switched "OFF", and while the ultraviolet LEDs 221 being the pulse UV emission mode with the wavelength of 260 is switched "ON" to perform the UV sterilization. Thereby, the ultraviolet LEDs 221 with the pulse UV emission mode and the wavelength with 275 nm and the ultraviolet LEDs 221 with the pulse UV emission mode and the wavelength with 260, this two groups of ultraviolet LEDs, perform the sterilization by ultraviolet light through successive alternating pluses.

The control module 5 further comprises a circuit board 54 and a control board 8, and the circuit board 54 comprises a plurality of light emitting diodes (LEDs) 52, a plurality of buttons 53, at least one connector 55 and a switch 56, and the control board 8 electrically connects to the circuit board 545 and the motor 10, the control board 8 comprises a connector 81, the connector 81 of the control board 8 is electrically connected to the connector 55 of the circuit board 5, and wherein there are many the light emitting diode (LED) holes 12 correspond to the light emitting diodes (LEDs) 52 mounted on the upper cover 1, and there are many button holes 11 correspond to the buttons 53 mounted on the upper cover 2. The circuit board 54 further comprises a negative ion generator 51, the negative ion generator 51 is arranged in inside of the diversion tube 7, and the negative ion generator 51 electrically connects the circuit board 54. The negative ion generator 51 can suppress dust mites, mildew, sterilization, virus killing, and deodorization.

The air purifier of the present invention connects to the power and the switch 56 on the air purifier is pressed, the control module 5 starts the motor 10 to operate, and when the motor 10 is in operation, external air enters into the air purifier through the filtering hole 31 of the filter cover 3, and the air is filtered through the filter films 41 of the filter 4 so as to filter contaminated particles in the air (e.g. dust, PM2.5). Then, when the filtered air through the gap between the filter 4 and the motor 10, the ultraviolet LEDs 221 use the ultraviolet light to sterilize the filtered air so as to generate the clean air. The clean air enters into the suction inlet 101 of the motor 10, and then the clean air flows out from the blow hole 71 of the diversion tube 7 to the column hole 20 to discharge the clean air. Therefore, the effect of purifying air and sterilizing can be achieved. The air purifier of the present invention, which has small size and portable, can be used for indoor space in the home or space in the car. The air purifier of the present invention further can filter harmful pollutants in the air and has both ultraviolet sterilization and negative ion generation to achieve various functions of purifying air. The air purifier of the present invention further uses the display of the LED 52 to help the user to monitor the usage state of the air purifier, and use the operation setting of the button 53 to control the operation speed of the motor 10 to adjust the airflow output, switch the functions of the ultraviolet sterilization and negative ion generation so as to achieve the intelligent monitoring results.

Figure 6:
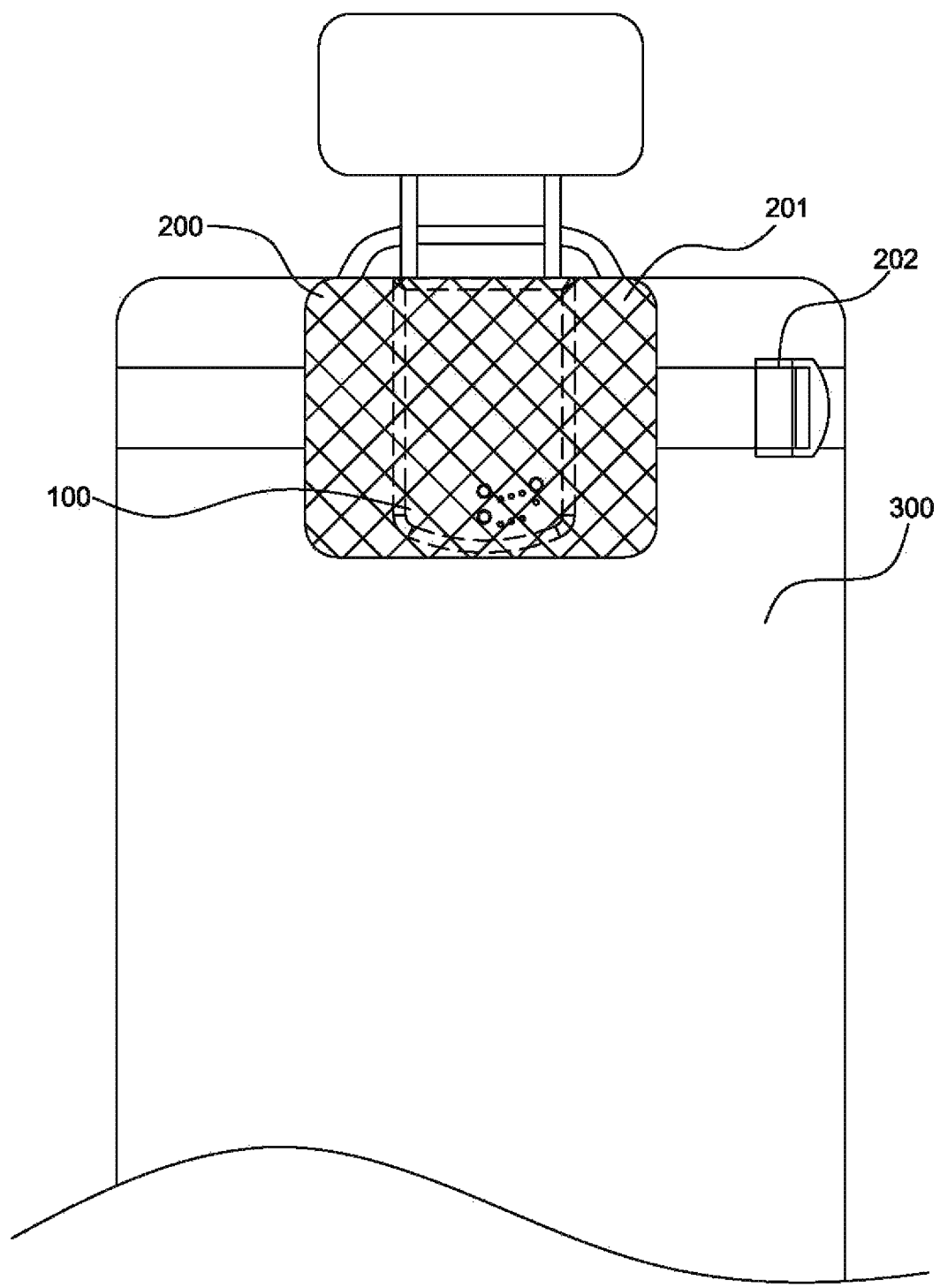
FIG. 6 illustrates a usage state schematic diagram of an air purifier placed in a bag according to one embodiment of the present invention.

FIG. 6 illustrates a usage state schematic diagram of an air purifier placed in a bag according to one embodiment of the present invention. Refer to FIG. 6, and while see FIG. 1, the air purifier 100 of the present invention may be used in the car. The air purifier 100 comprises: a upper cover 1, having at least one grid column 21 on front terminal of the upper cover 1; a bottom cover 2, having at least one grid column 21 on front terminal of the bottom cover 2, wherein the grid column 21 on front terminal of the upper cover 1 is combined with the grid column 21 on front terminal of the bottom cover 2 to form a column hole 20 through which an air flows out; and two groups of ultraviolet LEDs 22, respectively having a heat sink 222 and a ultraviolet LED 221, wherein the ultraviolet LED 221 is mounted on the heat sink 222, and a wavelength range of the ultraviolet LED 221 is between 100 nm and 480 nm which is violet-blue light wavelength range; and a bag 200, having a hole, and a place in the hole, and the place inside correspond to the upper cover 1 and the bottom cover 2, and a plurality of through holes 201 arranged on a surface of the bag 200, the through holes 201 connecting to the place, and the air flowed out through the through hole 201 to the outside of the bag 200, and wherein there is a fixed element 202 mounted on outer surface of the bag, and the fixed element 202 fixes the bag 200 on a chair back 300 of a car chair. In one embodiment, the wavelength range of the two groups of ultraviolet LEDs is between 100 nm and 280 nm. In one embodiment, the wavelength of one of two groups of ultraviolet LEDs is 260 nm, and the wavelength of another group of ultraviolet LEDs is 280 nm. In one embodiment, the wavelength range of one of two groups of ultraviolet LEDs are between 100 nm and 280 nm, and the wavelength range of another group of ultraviolet LEDs are between 400 nm and 480 nm. In one embodiment, the wavelength of one of two groups of ultraviolet LEDs is 275 nm, and the wavelength of another group of ultraviolet LEDs is 405 nm which is violet-blue light wavelength range. The structure of the air purifier 100 is composed of the structures and parts of FIGS. 1 to 5.

The fixed element 202 is selected from one of the flexible band, a clip, a rope or a velcro. When the fixed element 202 is flexible band, the flexible force of the flexible band is used to abut the bag 200 against the chair back 300 of the car chair; when the fixed element 202 is clip, the clip is used to clip the bag 200 against the chair back 300 of the car chair; When the fixed element 202 is rope, the rope is used to tie up the bag 200 against the chair back 300 of the car chair; When the fixed element 202 is Velcro, the Velcro is used to fix the bag 200 against the chair back 300 of the car chair. The user can accommodate the bag 200 of the air purifier 100 by the fixing member 202 to be fixed to the chair back 300 of the car chair without shaking.

While the present invention has been particularly shown and described with reference to a preferred embodiment, it will be understood by those skilled in the art that various changes in form and detail may be without departing from the spirit and scope of the present invention.

What is claimed is:

1. An air purifier, comprising:
   a upper cover, having at least one grid column on front terminal of the upper cover;
   a bottom cover, having at least one grid column on front terminal of the bottom cover;
   two groups of ultraviolet light emitting diodes (LEDs), respectively having a heat sink and a ultraviolet light emitting diode (LED), wherein the ultraviolet LED is mounted on the heat sink, and a wavelength range of the ultraviolet LED is between 100 nm and 480 nm; and
   a filter cover, a filter, a motor, a control module, a power module and a diversion tube, wherein the filter cover, the motor, the control module, the power module and the diversion tube are mounted between the upper cover and the bottom cover, and arranged in sequence toward the column hole, wherein the filter is mounted between the filter cover and the motor, one side of the motor has a suction inlet, the suction inlet is adjacent to the filter, and another side of the motor is adjacent to the diversion tube, wherein the power module and the control module are mounted on outer surface of the diversion tube, the power module has a transformer, and the power module electrically connects to the control module and the motor, wherein two sides of an gap between the filter and the motor respectively has the two groups of ultraviolet LEDs, and the two groups of ultraviolet LEDs electrically connects to the control module;
   wherein the grid column on front terminal of the upper cover is combined with the grid column on front terminal of the bottom cover to form a column hole through which an air flow out.

2. The air purifier of claim 1, wherein the wavelength range of the two groups of ultraviolet LEDs is between 100 nm and 280 nm.

3. The air purifier of claim 2, wherein the wavelength of one of two groups of ultraviolet LEDs are 260 nm, and the wavelength of another group of ultraviolet LEDs are 280 nm.

4. The air purifier of claim 1, wherein the wavelength range of one of two groups of ultraviolet LEDs is between 100 nm and 280 nm, and the wavelength range of another group of ultraviolet LEDs is between 400 nm and 480 nm which is violet-blue light wavelength range.

5. The air purifier of claim 4, wherein the wavelength of one of two groups of ultraviolet LEDs are 275 nm, and the wavelength of another group of ultraviolet LEDs are 405 nm which is violet-blue light wavelength range.

6. The air purifier of claim 1, wherein the diversion tube has a support and blow hole, the support is adjacent to the motor, and the filter cover has a plurality of filtering holes, and inside of the filter consists of a plurality of filter films.

7. The air purifier of claim 1, wherein the control module further comprises a circuit board and a control board, and the circuit board comprises a plurality of light emitting diodes, a plurality of buttons, at least one connector and a switch, and the control board electrically connects to the circuit board and the motor, the control board comprises a connector, the connector of the control board is electrically connected to the connector of the circuit board, and wherein there are many the light emitting diode holes correspond to the light emitting diodes mounted on the upper cover, and there are many button holes correspond to the buttons mounted on the upper cover.

8. The air purifier of claim 7, wherein the circuit board further comprises a negative ion generator, the negative ion generator is arranged in inside of the diversion tube, and the negative ion generator electrically connects the circuit board.

9. An air purifier, comprising:
   a upper cover, having at least one grid column on front terminal of the upper cover;
   a bottom cover, having at least one grid column on front terminal of the bottom cover, wherein the grid column on front terminal of the upper cover is combined with the grid column on front terminal of the bottom cover to form a column hole through which an air flow out;
   two groups of ultraviolet LEDs, respectively having a heat sink and a ultraviolet LED, wherein the ultraviolet LED is mounted on the heat sink, and a wavelength range of the ultraviolet LED is between 100 nm and 480 nm;
   a bag, having a hole, and a place in the hole, and the place inside correspond to the upper cover and the bottom cover, and a plurality of through holes arranged on a surface of the bag, the through holes connecting to the place, and the air flowed out through the through hole to the outside of the bag, and wherein there is a fixed element mounted on outer surface of the bag, and the fixed element fixes the bag on a chair back of a car chair; and
   a filter cover, a filter, a motor, a control module, a power module and a diversion tube, wherein the filter cover, the motor, the control module, the power module and the diversion tube are mounted between the upper cover and the bottom cover, and arranged in sequence toward the column hole, wherein the filter is mounted between the filter cover and the motor, one side of the motor has a suction inlet, the suction inlet is adjacent to the filter, and another side of the motor is adjacent to the diversion tube, wherein the power module and the control module are mounted on outer surface of the diversion tube, the power module has a transformer, and the power module electrically connects to the control module and the motor, wherein two sides of an gap between the filter and the motor respectively has the two groups of ultraviolet LEDs, and the two groups of ultraviolet LEDs electrically connects to the control module.

10. The air purifier of claim 9, wherein the fixed element is selected from one of the flexible band, a clip, a rope or a velcro.

11. The air purifier of claim 9, wherein the wavelength range of the two groups of ultraviolet LEDs is between 100 nm and 280 nm.

12. The air purifier of claim 11, wherein the wavelength of one of two groups of ultraviolet LEDs are 260 nm, and the wavelength of another group of ultraviolet LEDs are 280 nm.

13. The air purifier of claim 9, wherein the wavelength range of one of two groups of ultraviolet LEDs is between 100 nm and 280 nm, and the wavelength range of another group of ultraviolet LEDs is between 400 nm and 480 nm which is violet-blue light wavelength range.

14. The air purifier of claim 13, wherein the wavelength of one of two groups of ultraviolet LEDs are 275 nm, and the wavelength of another group of ultraviolet LEDs are 405 nm which is violet-blue light wavelength range.

15. The air purifier of claim 9, wherein the diversion tube has a support and a blow hole, the support is adjacent to the motor, and the filter cover has a plurality of filtering holes, and inside of the filter consists of a plurality of filter films.

16. The air purifier of claim 9, wherein the control module further comprises a circuit board and a control board, and the circuit board comprises a plurality of light emitting diodes, a plurality of buttons, at least one connector and a switch, and the control board electrically connects to the circuit board and the motor, the control board comprises a connector, the connector of the control board is electrically connected to the connector of the circuit board, and wherein there are many the light emitting diode holes correspond to the light emitting diodes mounted on the upper cover, and there are many button holes correspond to the buttons mounted on the upper cover.

17. The air purifier of claim 16, wherein the circuit board further comprises a negative ion generator, the negative ion generator is arranged in inside of the diversion tube, and the negative ion generator electrically connects the circuit board.

* * * * *